United States Patent
Postolov et al.

(10) Patent No.: US 8,238,645 B2
(45) Date of Patent: Aug. 7, 2012

(54) INSPECTION SYSTEM AND A METHOD FOR DETECTING DEFECTS BASED UPON A REFERENCE FRAME

(75) Inventors: Yuri Postolov, Afula (IL); Menachem Regensburger, Shimshit (IL)

(73) Assignee: Camtek Ltd., Migdal Haemek (IL)

( * ) Notice: Subject to any disclaimer, the term of this patent is extended or adjusted under 35 U.S.C. 154(b) by 1033 days.

(21) Appl. No.: 12/064,358

(22) PCT Filed: Aug. 29, 2006

(86) PCT No.: PCT/IL2006/000994
§ 371 (c)(1),
(2), (4) Date: Jul. 1, 2008

(87) PCT Pub. No.: WO2007/026349
PCT Pub. Date: Mar. 8, 2007

(65) Prior Publication Data
US 2009/0110260 A1    Apr. 30, 2009

Related U.S. Application Data

(60) Provisional application No. 60/712,142, filed on Aug. 30, 2005, provisional application No. 60/712,143, filed on Aug. 30, 2005, provisional application No. 60/712,144, filed on Aug. 30, 2005.

(51) Int. Cl.
*G06K 9/00* (2006.01)

(52) U.S. Cl. ......... 382/149; 382/141; 382/145; 382/144
(58) Field of Classification Search ................. None
See application file for complete search history.

(56) References Cited

U.S. PATENT DOCUMENTS

| 5,495,535 | A  | * | 2/1996  | Smilansky et al. | ........... 382/145 |
| 6,826,298 | B1 | * | 11/2004 | O'Dell et al.    | ................ 382/149 |

OTHER PUBLICATIONS

WIPO Search Report WO 2007/26349.

* cited by examiner

*Primary Examiner* — Jason M Repko
*Assistant Examiner* — Siamak Harandi
(74) *Attorney, Agent, or Firm* — Reches Patents

(57) ABSTRACT

A method for inspecting objects and an inspection system, the system includes: an image acquisition unit adapted to acquire multiple images, according to a predefined image acquisition scheme, of multiple portions of a diced wafer that comprises multiple dice; and a processor adapted to locate multiple unique features within the multiple images, at least partially during the acquisition of images; associate multiple unique features with multiple dice, at least partially during the location of multiple unique features; determine multiple transformations between multiple die coordinate systems and a global coordinate system, in response to a locations of unique features and their associations with multiple dice, at least partially during an association between multiple unique features with multiple dice; and detect defects in response to a comparison between dice and corresponding reference dice, in response to the transformations, at least partially during the determination of the multiple transformations.

18 Claims, 9 Drawing Sheets

INSPECTION SYSTEM AND A METHOD FOR DETECTING DEFECTS BASED UPON A REFERENCE FRAME

RELATED APPLICATIONS

This application claims the priority of U.S. provisional patents Ser. No. 60/712,144, titled "Wafer Mapping and Die Alignment for Post Diced Wafer with Non Linear Distortion of Dice", U.S. provisional patents Ser. No. 60/712,143, titled "Automatic die-model creation and wafer mapping for on-line wafer inspection and random retrieval of die-model data" and U.S. provisional patents Ser. No. 60/712,142, titled "Automatic Visual Inspection of Post Diced Wafer Placed on a Grid", all filed on 30 Aug. 2005.

FIELD OF THE INVENTION

This application relates to methods for inspecting diced wafers and a pipelined inspection system.

BACKGROUND OF THE INVENTION

Integrated circuits are manufactured by a highly complex and costly manufacturing process. During the first stages of this process a wafer is formed. A wafer includes multiple dice that are arranged in an ordered array of dice wherein the dice are parallel to each other, as illustrated in FIG. 1. Rectangular-shaped dice are arranged in columns and rows and are separated by scribe lines. The dice are characterized by a die X axis pitch 26 and a die Y axis pitch Y 28. Referring to FIG. 1, wafer 11 includes multiple dice 12(0,0)-12(k,j) that are collectively denoted 12. FIG. 1 also illustrates a global coordinate system 20 that includes X-axis 22 and Y-axis 24. The dice are arranged in parallel to these imaginary axes and are aligned with global coordinate system 20.

During the final manufacturing stages of the wafer the wafer is diced (or sawn) in order to separate between the different dice. The wafer is usually placed on a tape and after the dicing process the dice are then pulled away from each other, conveniently by using an ideally radial force. FIG. 2 illustrates a diced wafer 13, tape 37 and the forces (illustrated by arrows 35) that expand the diced wafer.

The sawing as well as the dice separation process result in a non-linear spatial relationships between the dice of the diced wafer. Each die can be shifted, rotated, sheered and stretched in relation to its previous (pre-dice) position and in relation to adjacent dice.

FIG. 3 illustrates an exemplary diced wafer 13. The dice (collectively denoted 14) of diced wafer 13 are not parallel to each other and diced wafer 13 is also misaligned (rotated) in relation to global coordinate system 20. The latter rotation can result from angular misalignments as well as mechanical inaccuracies.

Wafers and diced wafers are inspected for defects. The inspection can involve comparing between a die and a reference die. The following patents, all being incorporated herein by reference, illustrate various wafer inspection devices and methods as well as registration and alignment methods: U.S. Pat. No. 5,610,102 of Gardopee et al., U.S. Pat. No. 6,021,380 of Fredriksen et al., U.S. Pat. No. 6,937,753 of O'Dell et al., and U.S. Pat. No. 6,324,298 of O'Dell et al., and U.S. Pat. No. 4,981,529 of Tsujita.

Various prior art diced wafer inspection methods included locating a unique feature, comparing its location to an expected location, changing the scanning pattern in response to the differences between the actual location to the expected location and continuing to the next expected location of the unique feature.

There is a need to provide an inspection system that can inspect diced wafers and a method for inspecting diced wafers.

SUMMARY OF THE INVENTION

A method for inspecting a diced wafer that comprises multiple dice, the method includes: acquiring multiple images of multiple portions of the diced wafer according to a predefined image acquisition scheme; locating unique features within the multiple images, at least partially during the acquiring; associating multiple unique features with multiple dice, at least partially during the locating, determining multiple transformations between multiple die coordinate systems and a global coordinate system, in response to a locations of unique features and their associations with multiple dice, at least partially during the associating; and detecting defects in response to a comparison between dice and corresponding reference dice, in response to the transformations, at least partially during the determining.

An inspection system, the system includes: an image acquisition unit adapted to acquire multiple images, according to a predefined image acquisition scheme, of multiple portions of a diced wafer that comprises multiple dice; and a processor adapted to locate multiple unique features within the multiple images, at least partially during the acquisition of images; associate multiple unique features with multiple dice, at least partially during the location of multiple unique features; determine multiple transformations between multiple die coordinate systems and a global coordinate system, in response to a locations of unique features and their associations with multiple dice, at least partially during an association between multiple unique features with multiple dice; and detect defects in response to a comparison between dice and corresponding reference dice, in response to the transformations, at least partially during the determination of the multiple transformations.

BRIEF DESCRIPTION OF THE DRAWINGS

The present invention will be understood and appreciated more fully from the following detailed description taken in conjunction with the drawings in which.

DETAILED DESCRIPTION OF THE DRAWINGS

Various embodiments of the invention are herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Conveniently, a pipelined inspection system and a pipelined method are provided. The throughput of the system and method can be increased by performing multiple processing stages in parallel.

Multiple images are acquired conveniently according to a predefined image acquisition scheme that defines diced wafer scanning patterns. During the acquisition at least one processing stage is executed. The method does not require stopping the scanning process in order to adjust the scanning pattern in response to differences between an actual location of a unique feature and the expected location of this feature.

In addition, the scanning pattern can start at any location of the diced wafer, and not necessarily start from a predefined location such as the upper left end of the diced wafer.

According to an embodiment of the invention the predefined image acquisition scheme includes defining a certain scanning pattern that is not altered in response to detections of unique features, or even during defect detection. Scanning patterns can include raster scan patterns but this is not necessarily so.

Figure 1:
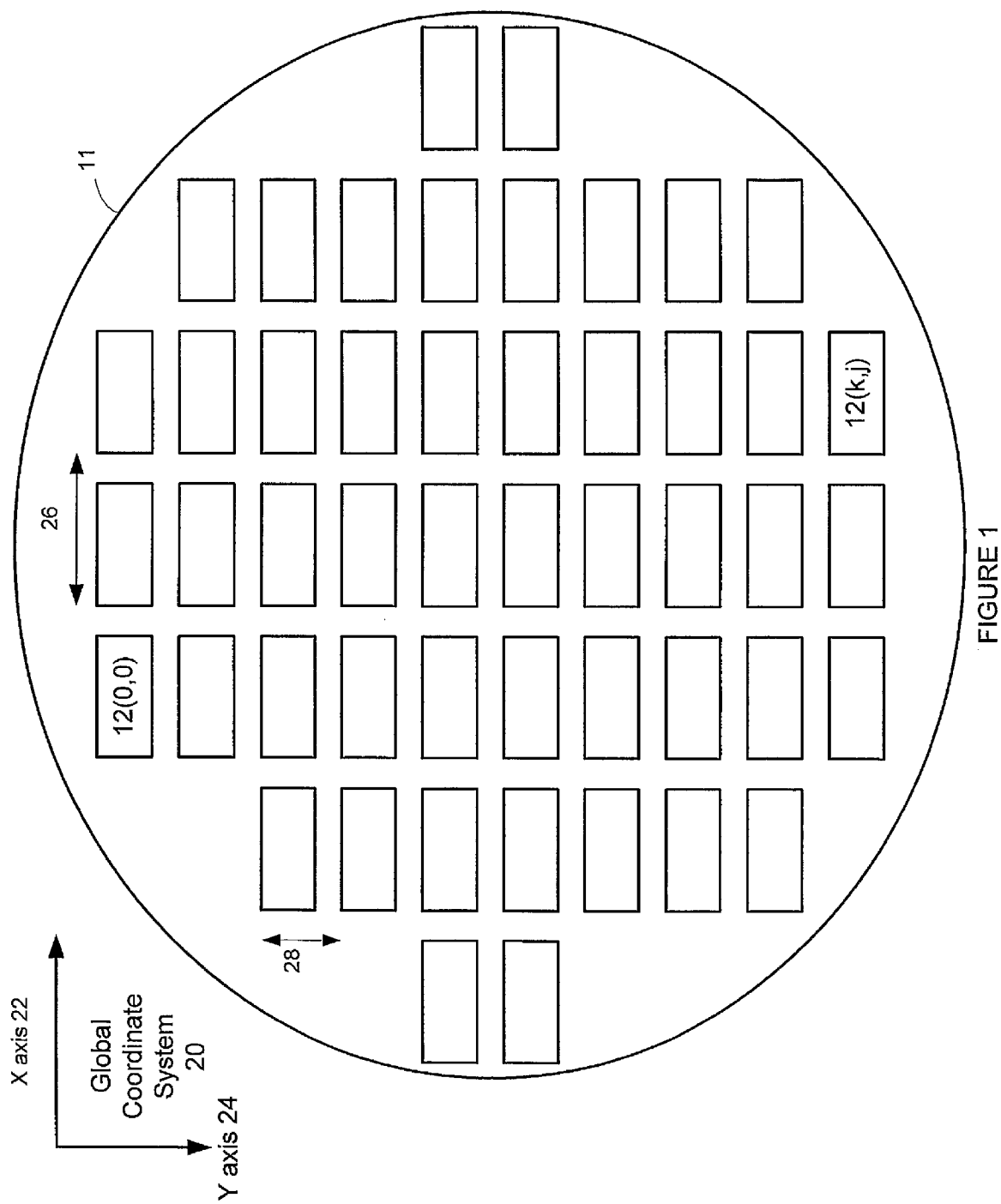
FIG. 1 illustrates a prior art wafer.
Figure 2:
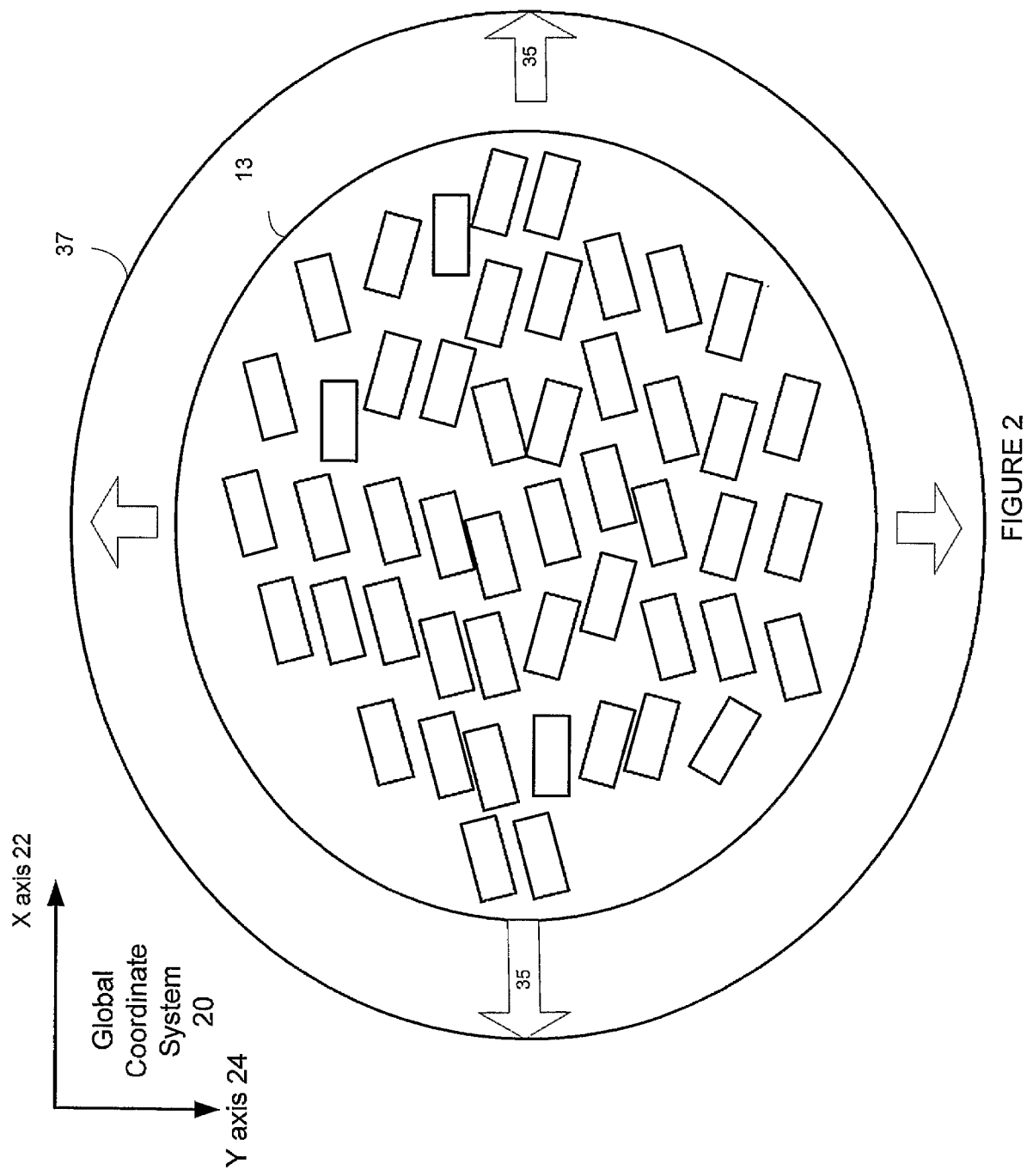
FIG. 2 illustrates a prior art diced wafer and the forces that expand the diced wafer.
Figure 3:
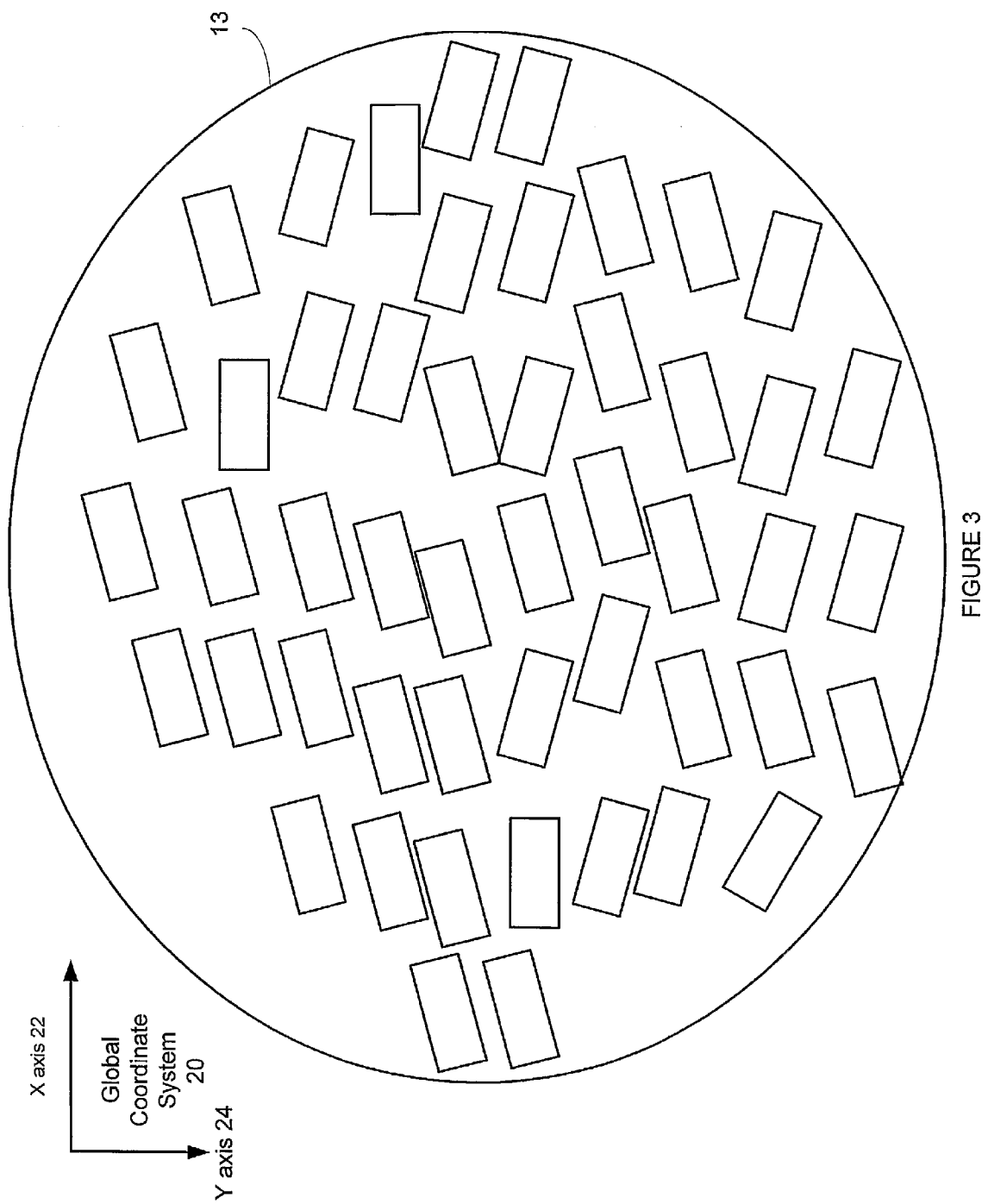
FIG. 3 illustrates a prior art diced wafer.
Figure 4:
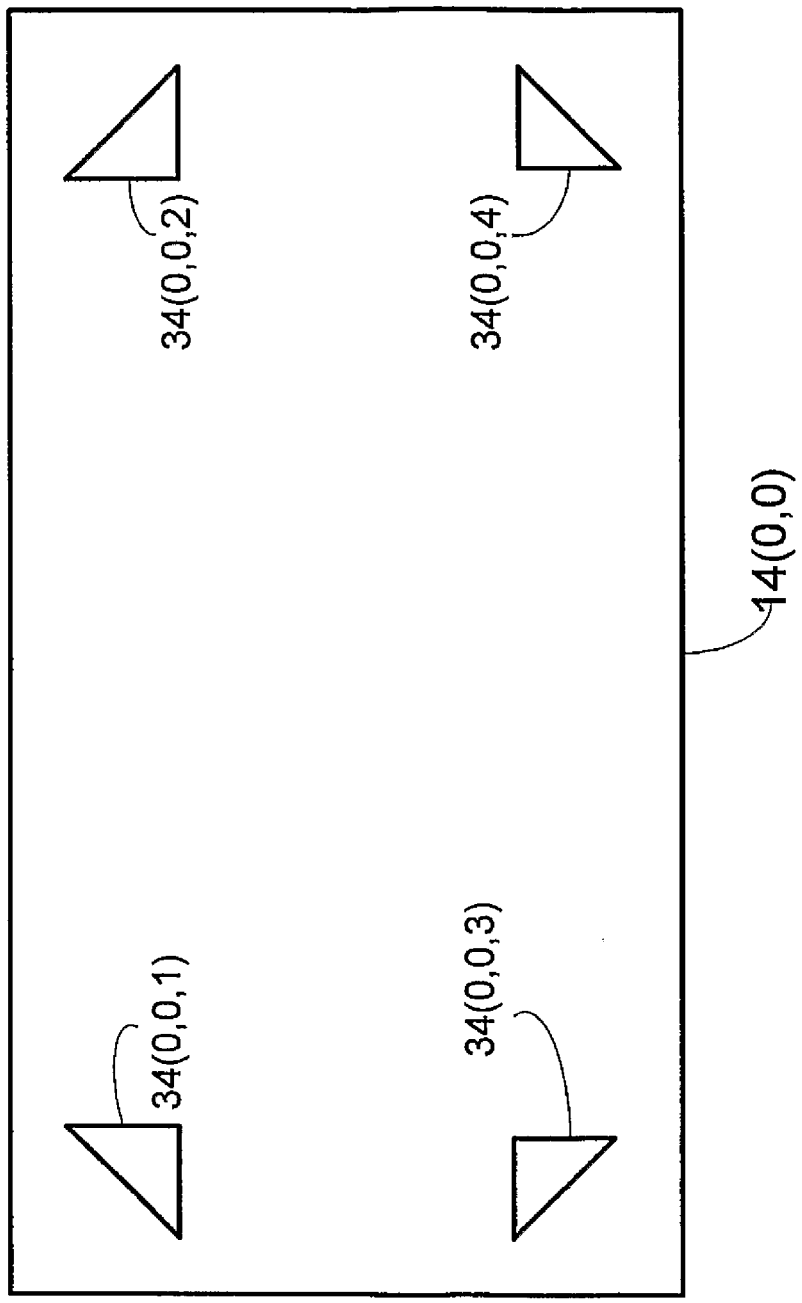
FIG. 4 illustrates a die that includes multiple unique features.

FIG. 4 illustrates a die 14(0,0) that includes four unique features 34(0,0,1)-34(0,0,4). These unique features are not removed due to the dicing process. Once two or more unique features are identified the orientation of die 14(0,0) as well as its position can be determined.

Figure 5:
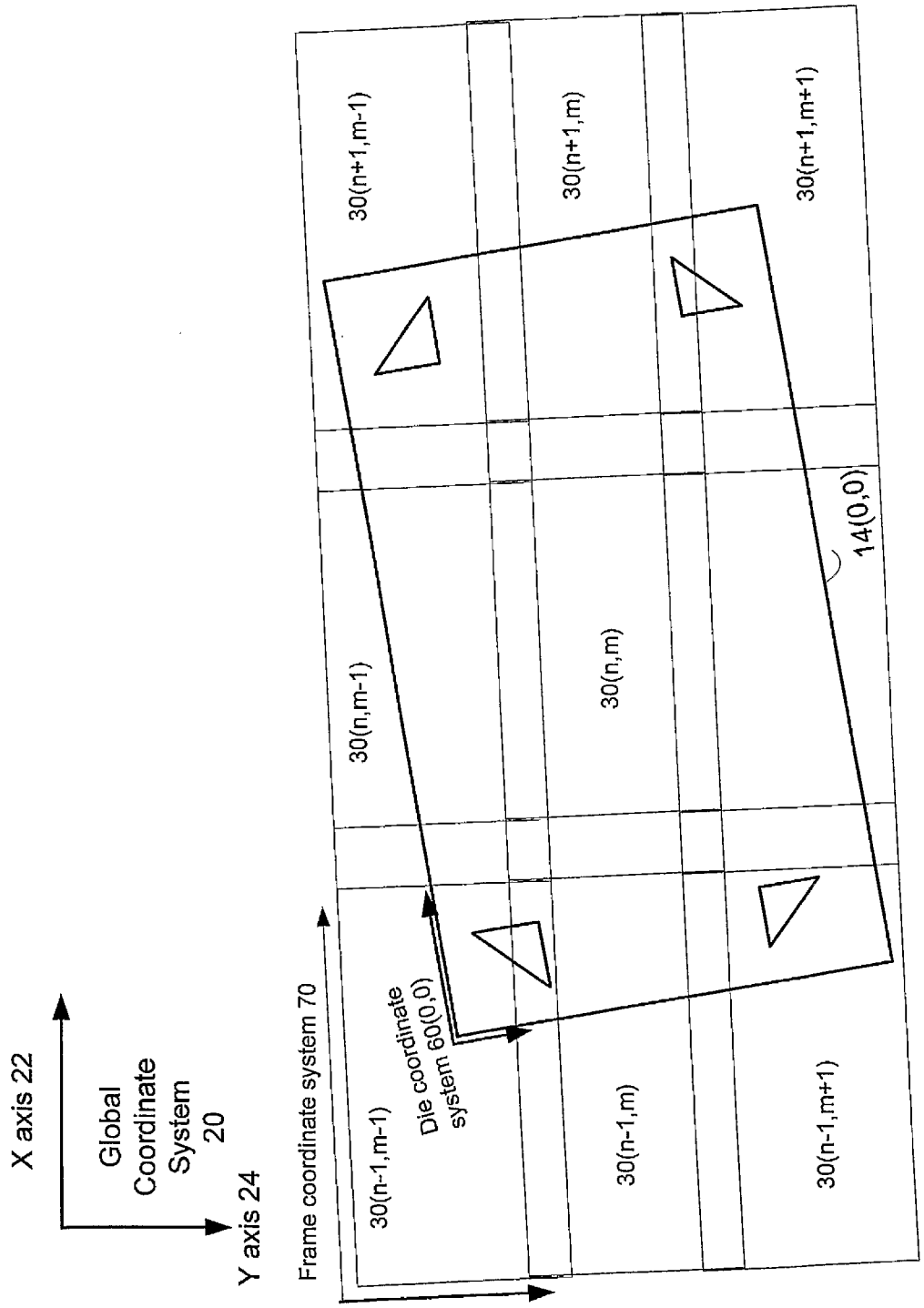
FIG. 5 illustrates multiple images, a die and three coordinate systems according to an embodiment of the invention.

FIG. 5 illustrates multiple images 30($n$−1,m)-30($n$+1, m+2), die 14(0,0) and three coordinate systems according to an embodiment of the invention.

Die 14(0,0) defines a die coordinate system 60(0,0). Each die of diced wafer 13 defines its own coordinate system. These die coordinate systems are usually not aligned with global coordinate system 20.

FIG. 5 also illustrates multiple images (also referred to as frames) that represent the images that are acquired by an image acquisition unit. These images are aligned with a frame coordinate system 70. Conveniently, the different die coordinate systems are not aligned with the frame coordinate system 70. Frame coordinate system 70 can be aligned with global coordinate system 20 but this is not necessarily so, as illustrated by FIG. 5. This misalignment can result from mechanical inaccuracies of the inspection system as well as from other reasons. Typically, the spatial relationship between global coordinate system 20 and frame coordinate system 70 can be determined during a calibration sequence of the inspection system.

FIG. 5 illustrates by set of 3×3 images 30($n$−1,m−1)-30($n$+1, m+1) that cover die 14(0,0) as well as its proximate vicinity. FIG. 5 illustrates that images 30($n$−1,m−1) includes unique feature 34(0,0,1), image 30($n$+1, m−1) includes unique feature 34(0,0,2), image 30($n$−1, m+1) includes unique feature 34(0,0,3) and image 30($n$+1, m+1) includes unique feature 34(0,0,4). Image (n−1,m) includes a part of unique feature 34(3,3,1) and image 30($n$+1,m) includes a part of unique feature 34(0,0,4).

Figure 6:
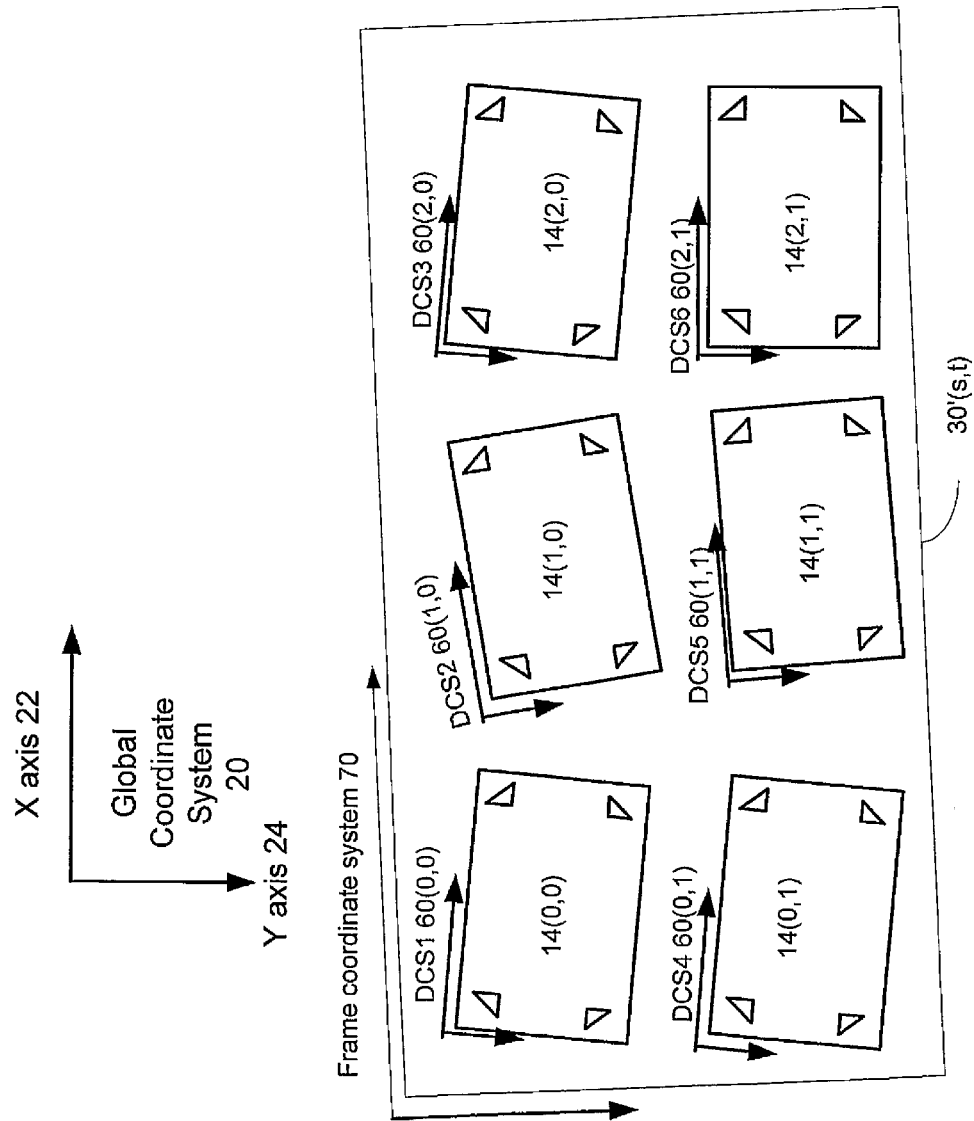
FIG. 6 illustrates an acquired image and multiple images of dices according to an embodiment of the invention.

FIG. 6 illustrates image 30' (s,t) that includes images of multiple dice 14(0,0)-14(2,1). Dice 14(0,0)-14(2,1) are associated with multiple die coordinate systems denoted DCS1-DCS6 60(0,0)-60(2,1). These die coordinate systems are not aligned to each other. Each die coordinate system is characterized by a transformation between it and a global coordinate system. The transformation can be calculated after two or more unique features that belong to the same die are located. The calculation can include: (i) determining the relationships between frame coordinate system 70 to each die coordinate system, and (ii) calculating a transformation between each die coordinate system and a global coordinate system in response: (a) a spatial relationship between the frame coordinate system and the global coordinate system, and (b) the relationships between the frame coordinate system and each of the die coordinate systems.

Figure 7:
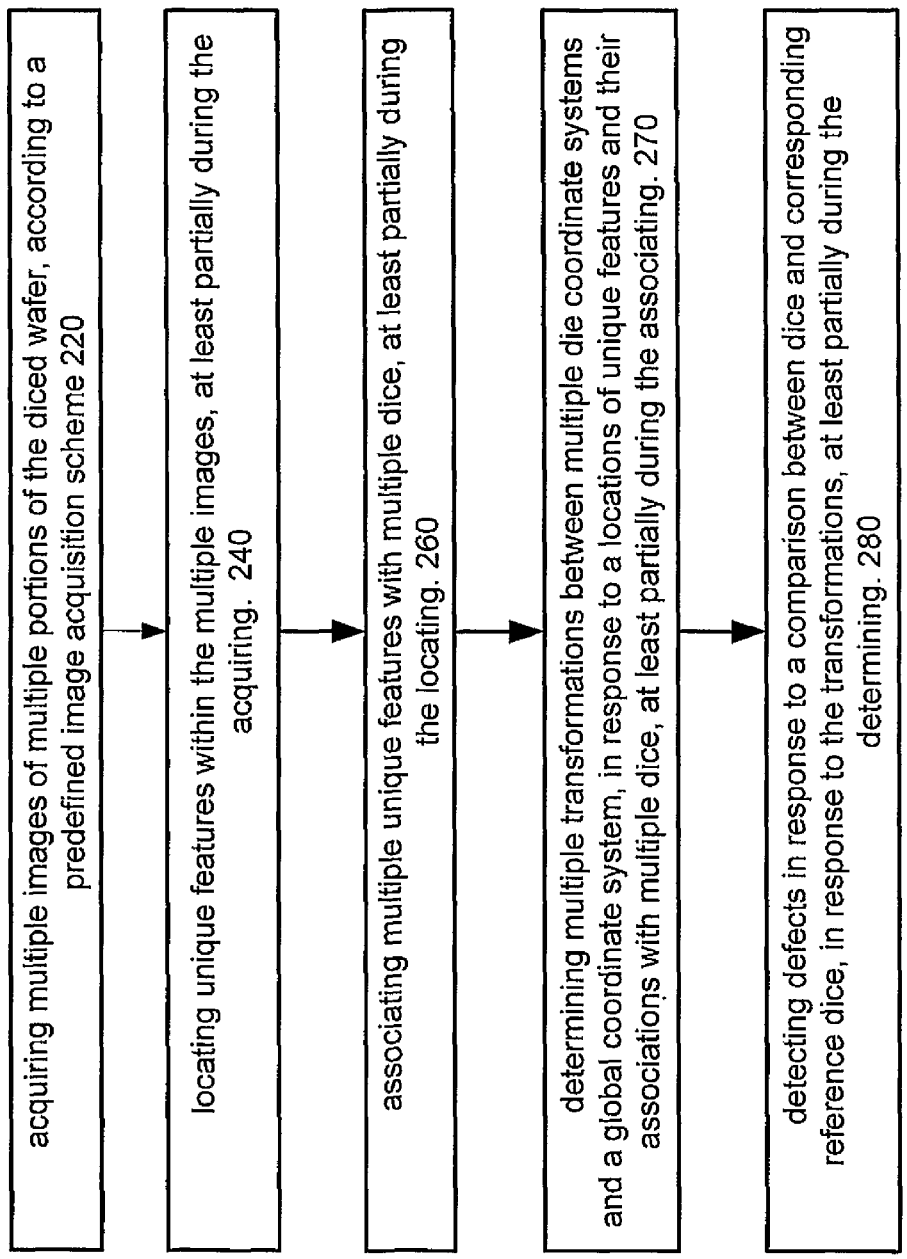
FIG. 7 illustrates a method for inspecting a wafer according to an embodiment of the invention.

FIG. 7 illustrates method 200 for inspecting a diced wafer, according to an embodiment of the invention.

Method 200 includes stages 220-280. For convenience of explanation FIG. 7 illustrates stages 220-280 as being arranged in a sequential order. It is noted that at least each pair of adjacent stages at least partially overlap. It is further noted that FIG. 7 illustrates a pipelined process that allows a performance of multiple tasks in parallel.

Method 200 starts by stage 220 of acquiring multiple images of multiple portions of the diced wafer according to a predefined image acquisition scheme.

It is noted that stage 220 can include illuminating the dice wafer by a continuous light source, by a pulsed light source, and an area illumination, by a spot light source, by applying bright field detection or dark field detection and the like.

Conveniently, stage 220 includes acquiring partially overlapping images.

Conveniently, stage 220 includes acquiring at least one acquired image that include images of multiple dice.

Conveniently, stage 220 includes acquiring at least one acquired image that includes only a portion of die. It this case an image of a single die can be reconstructed from multiple acquired images.

Stage 240 includes locating unique features within the multiple images. Stage 240 is executed at least partially during an execution of stage 220. In other words, while new images are acquired the method locates unique features of already acquired images.

Conveniently, stage 240 includes applying normalized correlation or geometric hashing. Geometric hashing is described in the following articles and patents, all being incorporated herein by reference: "Rehashing for Bayesian Geometric Hashing", M. Lifshits, I. Blayvas, R. Goldenberg and E. Rivlin, Proceedings of the 17$^{th}$ international conference on pattern recognition (ICPR'04), "Geometric Hashing: An Overview, H. J. Wolfson and I. Rigoutsos, IEEE Computational Science & Engineering, 1997 IEEE, U.S. Pat. No. 6,941,016 of Wagman et al., U.S. Pat. No. 7,027,651 of Simon et al., and U.S. Pat. No. 6,993,192 of Silver.

Conveniently, stage 240 includes applying multiple image recognition techniques.

Stage 260 includes associating multiple unique features with multiple dice. Stage 260 is executed at least partially during the execution of stage 240. In other words, while new unique features are located the method associates dice with already located unique features.

Conveniently, an execution of stage 260 at least partially overlaps an execution of stage 220.

Conveniently, stage 260 includes determining positions of multiple dice in response to locations of the multiple unique features and in response to and at least one die uncertainty parameter.

Conveniently, stage 240 includes locating each unique feature within an acquired image and storing located unique feature information and stage 260 includes retrieving located unique feature information and processing the retrieved unique feature information at least partially during the locating and storing.

Stage 270 includes determining multiple transformations between multiple die coordinate systems and a global coordinate system, in response to locations of unique features and their associations with multiple dice. Stage 270 is executed at least partially during the execution of stage 260. In other words, while new unique features are associated with new dice located the method determines the transformations between dice that were already associated with located unique features.

Conveniently, an execution of stage 270 at least partially overlaps an execution of stage 240. Conveniently, an execution of stage 270 at least partially overlaps an execution of stage 220.

Stage 280 includes detecting defects in response to a comparison between dice and corresponding reference dice, in response to the transformations. Stage 280 is executed at least partially during the execution of stage 270. In other words, while new transformations are determined the method detects defects in dice that are characterized by a calculated transformation between their coordinate system and a global coordinate system.

Conveniently, an execution of stage 280 at least partially overlaps an execution of stage 260. Conveniently, an execution of stage 280 at least partially overlaps an execution of stage 240. Conveniently, an execution of stage 280 at least partially overlaps an execution of stage 220.

Conveniently, method 200 includes defining of a die coordinate system in view of located unique feature information at least partially during the associating, if the die coordinate system can be defined in view of located unique feature information representative of at least one located unique feature.

Figure 8:
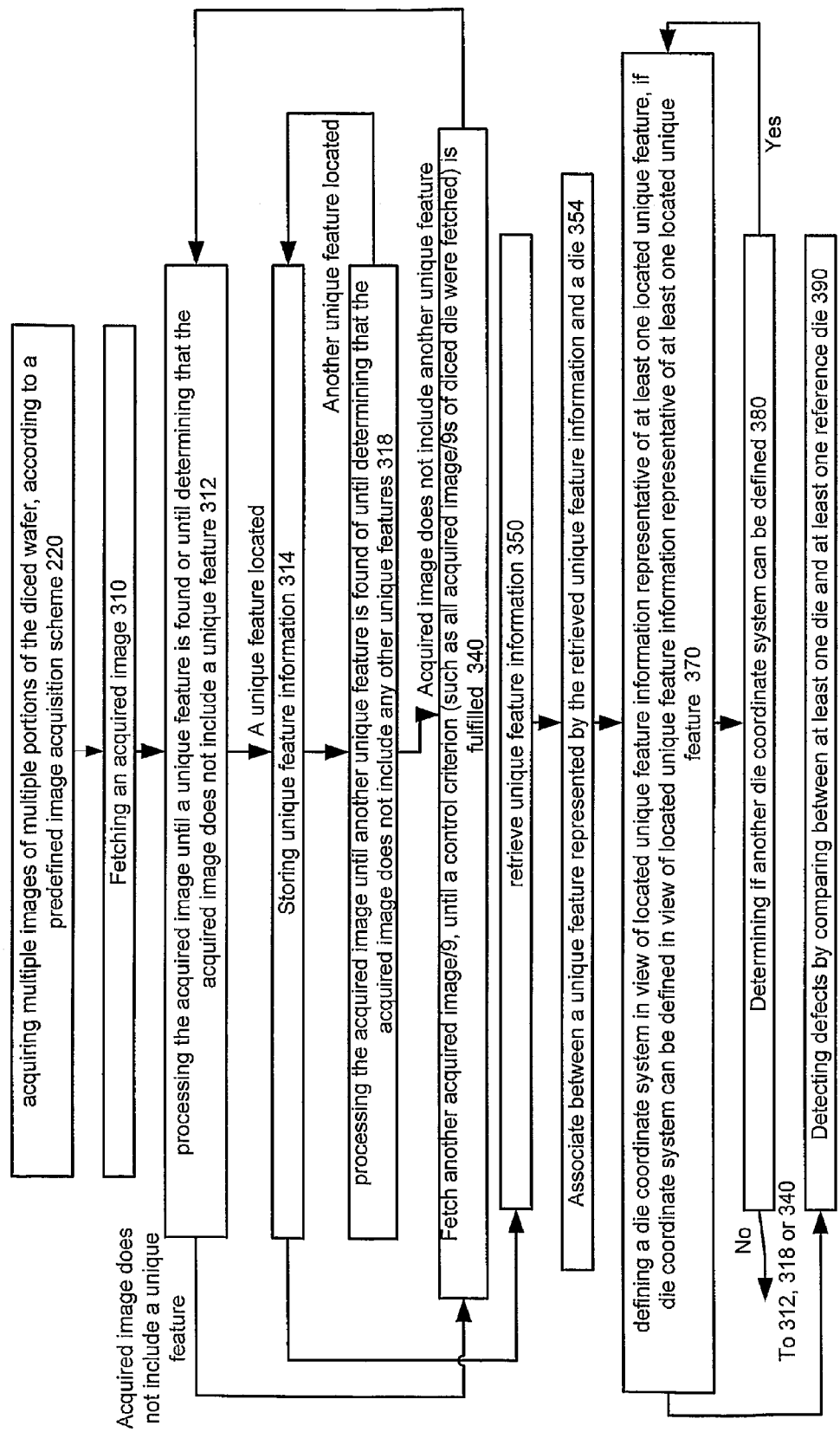
FIG. 8 illustrates a sequence of stages according to an embodiment of the invention.

FIG. 8 illustrates sequence 300 of stages according to an embodiment of the invention.

Sequence 300 starts by stage 220 of acquiring multiple images of multiple portions of the diced wafer according to a predefined image acquisition scheme.

After at least one image is acquired stage 310 is executed. Stage 310 includes fetching an acquired image.

Stage 310 is followed by stage 312 of processing the fetched acquired image until a first unique feature is found or until determining that the acquired image does not include any unique feature.

If a unique feature was found then stage 312 is followed by stage 314 of storing unique feature information. Else, stage 312 is followed by stage 340.

Stage 314 is followed by stage 318 of processing the acquired image until another unique feature is found or until determining that the acquired image does not include another unique feature.

If another unique feature is found stage 318 is followed by stage 314. Else, stage 318 is followed by stage 340.

Stage 340 includes fetching another acquired image until a control criterion (such as all acquired images of a diced wafer were acquired) is fulfilled.

Stage 314 is also followed by stage 350 of retrieving unique feature information. Stage 350 is followed by stage 354 of associating between at least one unique feature that is represented by the retrieved unique feature information and a die. The association can include checking if a newly located unique feature belongs to an already found die or whether is belongs to a die that was not found yet. This determination can be responsive to the locations of previously located dice, to dice dimensions (or die pitch) as well as to uncertainties associated with the dicing and expansion process.

Stage 354 is followed by stage 370 of defining a die coordinate system in view of located unique feature information representative of at least one located unique feature, if die coordinate system can be defined in view of located unique feature information representative of at least one located unique feature.

Stage 370 is followed by stages 380 and 390. Stage 380 includes determining if another die coordinate system can be defined. If the answer is positive stage 380 is followed by stage 370, else stage 380 can be followed by any one of the following stages 312, 318 or 340.

Stage 390 includes detecting defects by comparing between at least one die and at least one reference die. Stage 390 includes comparing between multiple pixels of an acquired image and multiple reference pixels that correspond to the same location of the die and reference die.

Figure 9:
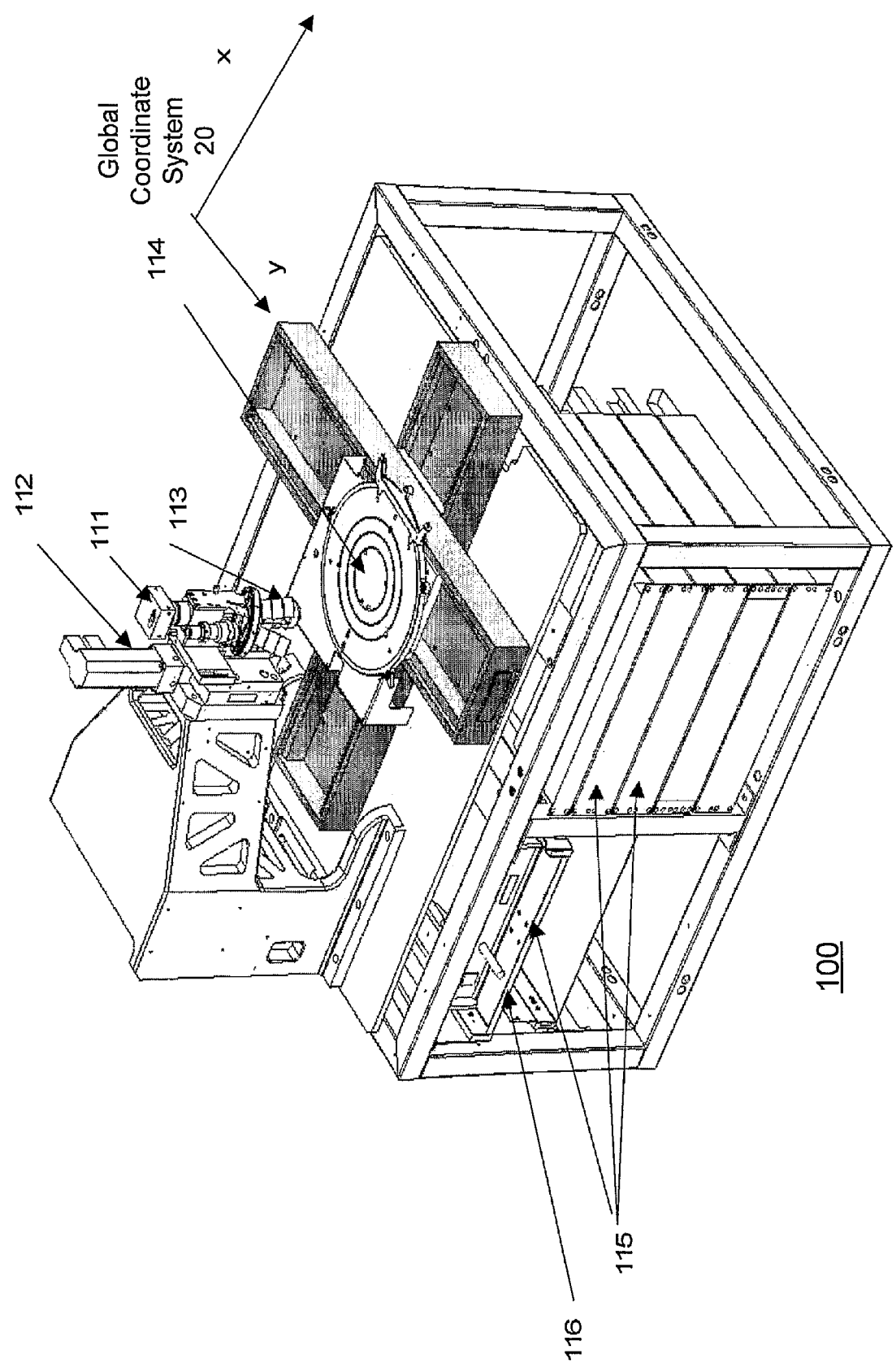
FIG. 9 illustrates a pipelined inspection system, according to an embodiment of the invention.

FIG. 9 illustrate system 100 according to an embodiment of the invention. System 100 includes image acquisition unit 111, processor 115, illuminator 112, optics 113, a mechanical stage such as X-Y table 114 and storage unit 116.

System 100 can define or receive a predefined image acquisition scheme and accordingly scan the diced wafer while acquiring images.

X-Y table 114 is adapted to introduce a continuous mechanical translation between the diced wafer and the image acquisition unit.

Image acquisition unit 111 can include one or more detectors that can acquire an image of an area illuminated by illuminator 112. Optics 13 may serve the illumination of a diced wafer (placed on X-Y table 114) as well as serve for collecting light and directing it towards image acquisition unit 111. Storage unit 116 stored acquired images and is accessible by processor 115. It is noted that the detection signals from image acquisition unit 111 can be processed by processor 115 in order to provide images (or frames).

The diced wafer can be illuminated by overlapping strobes of light that forming overlapping images of frames.

The motion of X-Y table 114 is managed electronically by high precision control system, this enables to correlate the exact location of each pixel in the scanned object (image) in relation to global coordinate system 20.

Conveniently, image acquisition unit 112 is adapted to acquire multiple images of multiple portions of a diced wafer that include multiple dice while processor 115 is adapted to: (i) locate multiple unique features within the multiple images, at least partially during the acquisition of images; (ii) associate multiple unique features with multiple dice, at least partially during the location of multiple unique features; (iii) determine multiple transformations between multiple die coordinate systems and a global coordinate system, in response to a locations of unique features and their associations with multiple dice, at least partially during an association between multiple unique features with multiple dice; and (iv) detect defects in response to a comparison between dice and corresponding reference dice, in response to the transformations, at least partially during the determination of the multiple transformations.

Conveniently, processor 115 is adapted to execute at least one of the following operations, or a combination thereof: (i)

determine positions of multiple dice in response to locations of the multiple unique features and in response to and at least one die uncertainty parameter; (ii) locate each unique feature within an acquired image and store located unique feature information and to retrieve located unique feature information and process the retrieved unique feature information at least partially during the location of each unique feature and the storage of located unique feature information, (iii) define a die coordinate system in view of located unique feature information at least partially during the association between multiple unique features with multiple dice, if the die coordinate system can be defined in view of located unique feature information representative of at least one located unique feature, (iv) locate at least one unique feature by applying normalized correlation or geometric hashing, and (v) locate at least one unique feature by applying multiple image recognition techniques.

It is noted that memory unit 116 can also store images of the reference dice as well as information relating to the acquired images of the dice of the diced wafer. It can store a reference wafer map, and alternatively or additionally the diced wafer map.

Image acquisition unit 111 can include one or more line sensors, point sensors, two dimension sensor arrays and the like. Illuminator 112 can include a laser source a lamp, can provide light pulses or continuous illumination, can illuminate a spot or illuminate an area. Illuminator 112 is illustrated as bright field illuminator but system 100 can apply, additionally or alternatively, dark filed illumination.

Processor 115 can also control the operation of the various components of system 100 but this is not necessarily so and system 100 can include one or other controllers that control the operation of system 100.

Conveniently, storage unit 116 may include one or multiple storage components that be accessed serially or in a parallel manner, for speeding to processing speed of system 100. Different storage unit components can store different type of information or the same type of information.

Although the invention has been described in conjunction with specific embodiments thereof, it is evident that many alternatives, modifications and variations will be apparent to those skilled in the art, accordingly, it is intended to embrace all such alternatives, modifications and variations that fall within the spirit and broad scope of the appended claims.

We claim:

1. A method for inspecting a diced wafer that comprises multiple dice, the method comprises: acquiring multiple images of multiple portions of the diced wafer according to a predefined image acquisition scheme; wherein the multiple images are aligned with a frame coordinate system; locating unique features within the multiple images, at least partially during the acquiring; associating multiple unique features with multiple dice, at least partially during the locating, determining multiple transformations between multiple die coordinate systems and a global coordinate system, in response to locations of unique features and their associations with multiple dice, at least partially during the associating; and detecting defects in response to a comparison between dice and corresponding reference dice, and in response to the transformations, at least partially during the determining; wherein the determining of the multiple transformations between multiple die coordinate systems and a global coordinate system comprises (i) determining the relationships between the frame coordinate system to each die coordinate system, and (ii) calculating a transformation between each die coordinate system and the global coordinate system in response to: (a) a spatial relationship between the frame coordinate system and the global coordinate system, and (b) the relationships between the frame coordinate system and each of the die coordinate systems.

2. The method according to claim 1 wherein the associating comprises determining positions of multiple dice in response to locations of the multiple unique features and in response to and at least one die uncertainty parameter.

3. The method according to claim 1 wherein the locating comprises locating each unique feature within an acquired image and storing located unique feature information; wherein the stage of associating comprises retrieving located unique feature information and processing the retrieved unique feature information at least partially during the locating and storing.

4. The method according to claim 1 wherein the method comprises defining of a die coordinate system in view of located unique feature information at least partially during the associating, if the die coordinate system can be defined in view of located unique feature information representative of at least one located unique feature.

5. The method according to claim 1 wherein the acquiring comprises introducing a continuous mechanical translation between the diced wafer and an image acquisition unit.

6. The method according to claim 1 wherein the locating comprises applying normalized correlation or geometric hashing.

7. The method according to claim 1 wherein the locating comprises applying multiple image recognition techniques.

8. The method according to claim 1 wherein a single acquired image comprises images of multiple dice.

9. The method according to claim 1 wherein a single acquired image comprises a portion of an image of a die.

10. An inspection system, the system comprises: an image acquisition unit adapted to acquire multiple images, according to a predefined image acquisition scheme, of multiple portions of a diced wafer that comprises multiple dice; wherein the multiple images are aligned with a frame coordinate system; and a processor adapted to locate multiple unique features within the multiple images, at least partially during the acquisition of images; associate multiple unique features with multiple dice, at least partially during the location of multiple unique features; determine multiple transformations between multiple die coordinate systems and a global coordinate system, in response to locations of unique features and their associations with multiple dice, at least partially during an association between multiple unique features with multiple dice; and detect defects in response to a comparison between dice and corresponding reference dice, and in response to the transformations, at least partially during the determination of the multiple transformations; wherein the processor is arranged to determine the multiple transformations between multiple die coordinate systems and a global coordinate system by (i) determining the relationships between the frame coordinate system to each die coordinate system, and (ii) calculating a transformation between each die coordinate system and the global coordinate system in response to: (a) a spatial relationship between the frame coordinate system and the global coordinate system, and (b) the relationships between the frame coordinate system and each of the die coordinate systems.

11. The system according to claim 10 wherein the processor is adapted to determine positions of multiple dice in response to locations of the multiple unique features and in response to and at least one die uncertainty parameter.

12. The system according to claim 10 wherein the processor is adapted to locate each unique feature within an acquired image and store located unique feature information and to retrieve located unique feature information and process the retrieved unique feature information at least partially during the location of each unique feature and the storage of located unique feature information.

13. The system according to claim 10 wherein the processor is adapted to define a die coordinate system in view of located unique feature information at least partially during the association between multiple unique features with multiple dice, if the die coordinate system can be defined in view of located unique feature information representative of at least one located unique feature.

14. The system according to claim 10 wherein the system is adapted to acquire images while introducing a continuous mechanical translation between the diced wafer and the image acquisition unit.

15. The system according to claim 10 wherein the processor is adapted to locate at least one unique feature by applying normalized correlation or geometric hashing.

16. The system according to claim 10 wherein the processor is adapted to locate at least one unique feature by applying multiple image recognition techniques.

17. The system according to claim 10 wherein the image acquisition unit is adapted to acquire an image that comprises images of multiple dice.

18. The system according to claim 10 wherein the image acquisition unit is adapted to acquire an image that comprises a portion of an image of a die.

* * * * *